US010162934B2

(12) United States Patent
Nagahara et al.

(10) Patent No.: US 10,162,934 B2
(45) Date of Patent: Dec. 25, 2018

(54) DATA DE-DUPLICATION SYSTEM USING GENOME FORMATS CONVERSION

(71) Applicant: INTERNATIONAL BUSINESS MACHINES CORPORATION, Armonk, NY (US)

(72) Inventors: Rika Nagahara, Tokyo (JP); Yasushi Negishi, Tokyo (JP); Takeshi Ogasawara, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 408 days.

(21) Appl. No.: 14/954,316

(22) Filed: Nov. 30, 2015

(65) Prior Publication Data
US 2017/0154153 A1    Jun. 1, 2017

(51) Int. Cl.
G06F 17/30 (2006.01)
G06F 19/28 (2011.01)

(52) U.S. Cl.
CPC .................................. *G06F 19/28* (2013.01)

(58) Field of Classification Search
CPC ............ G06N 3/08; G06N 3/063; G06N 3/04; G06N 3/049; G06F 17/3033; G06F 17/30489; G06F 17/569; G06F 19/28; G06F 19/18; G06F 30/0241
See application file for complete search history.

(56) References Cited

U.S. PATENT DOCUMENTS

| 5,867,112 A * | 2/1999 | Kost .................. H04N 1/00204 341/51 |
| 8,364,644 B1 * | 1/2013 | Yadav ............... G06F 17/30088 707/649 |
| 2004/0083347 A1 * | 4/2004 | Parson .............. G06F 17/30949 711/165 |
| 2004/0086861 A1 * | 5/2004 | Omori ..................... G06F 19/22 435/6.14 |
| 2013/0311106 A1 * | 11/2013 | White ..................... G06F 19/20 702/20 |
| 2014/0280327 A1 * | 9/2014 | Pham ...................... G06F 19/18 707/770 |
| 2015/0149510 A1 * | 5/2015 | Kennedy ................. G06F 19/32 707/803 |

FOREIGN PATENT DOCUMENTS

WO    2011073680    6/2011

OTHER PUBLICATIONS

CRAM format specification (version 3.0), samtools-devel@lists.sourceforge.net, Jun. 1, 2015.
Sequence Alignment/Map Format Specification, The SAM/BAM Format Specification Working Group, Aug. 28, 2015.
(Continued)

*Primary Examiner* — Scott A. Waldron
*Assistant Examiner* — Fatima P Mina
(74) *Attorney, Agent, or Firm* — Tutunjian & Bitetto, P.C.; Vazken Alexanian (57) ABSTRACT

A computer-implemented method for data-deduplication of genome data that is in different file formats is described. Representative data from different genome file formats is conformed to a selected file format and compared. Duplicate files are identified and duplicate files are released, with at least one file copy being retained.

20 Claims, 6 Drawing Sheets

(56) References Cited

OTHER PUBLICATIONS

Alex Osuna, et al.. Implementing IBM Storage Data Deduplication Solutions, ibm.com/redbooks, Mar. 2011.
1000 Genomes, a Deep Catalog of Human Genetic Variation, http://www.1000genomes.org/.
The computational resources for large-scale genome analysis, The University of Tokyo Institute of Medical Science, 78th Annual Meeting of the Japanese Circulation Society Scientific Meeting, Mar. 21-23, 2014 (with translated portions).

* cited by examiner

DATA DE-DUPLICATION SYSTEM USING GENOME FORMATS CONVERSION

BACKGROUND

Technical Field

The present invention relates to bioinformatics, and more particularly to the size reduction of a genome database.

Description of the Related Art

Genome sequencing has been greatly enhanced by the development of next-generation sequencing techniques and advances in the machines that do the sequencing. Sequencing a human genome, which contains 3.2 billion base pairs, generates a massive amount of data that requires hundreds of gigabytes (GB) of storage space. The original plan of the 1000 Genomes project, launched in 2008, was to sequence the genomes of at least 1000 anonymous participants from different ethnic groups, using faster, less expensive technologies.

In 2012, the sequencing of 1092 genomes by the 1000 Genomes project was announced in Nature. Since then, administrators indicated that "as of March 2013, our ftp site is 464 TB [terabytes] and continuing to grow".

There are several data formats in which genome data is stored. The FASTQ format is a text-based format for storing a biological sequence (e.g., a nucleotide sequence) and corresponding quality scores. FASTQ encodes each of the sequence letters and the quality score with ASCII characters. FASTQ is the de facto standard for storing the output of high throughout sequencing devices, such as the Illumina® Genome Analyzer.

The FASTQ system is highly redundant as it reads sequence information within a sample and across samples, and many of the sequence reads consist of the same sequence. Different DNA formats make use of the FASTQ sequencing data, for example the SAM, BAM and CRAM file formats. These file formats require enormous amounts of computer storage space.

SUMMARY

With the understanding that it would be advantageous to eliminate redundancies in the stored genome data, described according to present principles is a computer-implemented method of data-deduplication of genome data in different file formats, in which the genome data files are stored in a computer memory, creating conformed representations in a selected genome file format of genome data derived from the original genome data files that represent the original genome data files, comparing the conformed representations of genome data, identifying duplicates among the conformed representations of genome data, retaining at least one of the duplicates of the original genome data files, and releasing at least one of the duplicates of the genome data files. In the computer-implemented method, one or more of the creating, comparing, identifying, retaining and releasing are performed by at least one hardware processor.

In accordance with present principles, described is a system for de-duplicating genome data that is in different genome file formats, comprising hardware processors having memory for storing genome files and for collecting sequence identification information and mandatory file field information from original genome data files in different genome file formats, the system having a generator for generating conformed representations of genome derived from the original genome data files, a comparer, for comparing the generated conformed representations of genome data derived from the original genome data files and for identifying duplicates among same, and a data de-duplicator for retaining at least one of the duplicates of the original genome data file and releasing at least one of the duplicates of the genome data files.

According to present principles, also described is a computer program product for de-duplicating genome data across different file formats, the computer program product being a computer readable storage medium having program instructions embodied therewith, the program instructions being executable by a computer to cause the computer to perform a method that includes creating, from genome data files, conformed representations in a selected genome file format of genome data derived from the original genome data files that represent the original genome data files, comparing the conformed representations of genome data, identifying duplicates among the conformed representations of genome data, retaining at least one of the duplicates of the original genome data files, and releasing at least one of the duplicates of the genome data files.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

The present principles are directed to systems and methods for de-duplicating data stored in different genome data file formats. Since genome files formats employ very large amounts of file storage capacity, the application of present principles releases significant amounts of duplicative data from system storage, effectively reducing the amount of data stored by a genome data file storage system while retaining a unique copy of all of the genome data stored prior to data-deduplication. For example, according to present principles, no unique genome file data is lost.

The Sequence Alignment/Map (SAM) genome file format is a human-readable text file that stores data in a series of tab delimited ASCII columns. SAM data may be output from aligners that read the FASTQ files and assign sequences to position with regard to a known reference genome. Each alignment line has 11 mandatory fields for essential alignment information such as mapping position, and a number of optional fields for flexible or aligner specific information.

The BAM genome file format is the binary equivalent to a SAM file. The BAM file stores the data of the SAM format in a compressed, indexed form in binary code. The BAM data is compressed in BGZF (Blocked GNU Zip Format). BGZF is block compression implemented on top of the standard gzip file format. BGZF provides good compression while allowing efficient random access to the BAM file for indexed queries.

CRAM genome file format is a restructured column-oriented binary container format. CRAM files are also encoded in binary. CRAM files are compressed versions of the SAM/BAM data in a different encoding. The CRAM data is based on the SAM data but has additional features allowing for more efficient data storage. In contrast to BAM, CRAM uses bits as well as bytes for data storage so that various coding techniques which output variable length binary codes can be used directly in CRAM.

A number of different genome file formats, e.g., SAM files, BAM files and CRAM files, are processed by the present system. The files can be stored in a computer storage device, and in one embodiment, all of these files would be subject to data de-duplication in accordance with the present principles. In one embodiment, the formats are identified by their file extensions, e.g., .sam, .bam, and .cram. In another embodiment, a combination of these files may be stored and processed. The system and method according to present principles could be most effective in an embodiment in which all files across all formats are subject to the present principles.

The SAM, BAM and CRAM file formats store data in mandatory file fields and optional file fields. Regardless of the formats, unique sequence data having a unique sequence identification (ID) is stored in metadata (e.g., metadata information pertaining to the original file is stored in an fast accessible location, e.g., an address area). In other words, the sequence ID field is common to the SAM, BAM and CRAM file formats.

In one embodiment, the data is split in chunks by chunking, e.g., the breaking data into standardized units that can be examined for duplicates. Depending on various factors, these units can be files or blocks of files. In one embodiment, data chunking is done by one of the following data chunking methods: file-based, block-based, and format-aware. In file-based chunking, each chunk is a single file. In block-based chunking, the data object is chunked into blocks of fixed or variable size. Block-based de-duplication is used by block-storage devices. In format aware chunking, the data formats are understood by the system and data objects are chunked according to the format. For example, format aware chunking could break a file into file components, e.g., a file comprised of slides for a presentation into separate slides.

In one embodiment, hash values are computed for at least the mandatory file fields of the genome data files. In one embodiment, the hash values are computed for optional file fields of the genome data files as well. The computed hash value of the mandatory file fields is added to the sequence ID. This information is stored in metadata. In one embodiment, the mandatory file fields include information such as sequence alignment position information and quality score of the sequence. For example, the 11 mandatory file fields of the SAM file format are the (1) QNAME field; (2) FLAG field; (3) RNAME field; (4) POS field; (5) MAPQ field; (6) CIGAR field; (7) RNEXT field; (8) PNEXT field; (9) TLEN field; (10) SEQ field; and (11) QUAL field.

In one other embodiment, after the data is broken into chunks, the optional file fields are stored in a different area. Metadata information pertaining to the original file is stored in an fast accessible location, e.g., an address area. Pointers, if necessary, are established between the data chunk, e.g., file, and/or the stored optional fields and metadata. In one embodiment, the optional file fields are copied from the original file and the copy of the optional file fields is stored.

The metadata may include information for facilitating the re-converting of data, back into the original file format. Exemplary metadata categories include the sequence ID, pointers to converted mandatory fields and optional fields, and attribute information for conversion from CRAM back to the original file format, e.g., SAM and/or BAM. A file format de-conversion could involve decompression and/or conversion from binary code to ASCII code.

In one embodiment, the metadata includes information for facilitating the de-converting of a converted file to its original file format. For example, should a file be converted from a SAM file to a CRAM file, the metadata could be used in the de-conversion of the CRAM file to a SAM file. This could be advantageous in de-conversion because the optional file fields in the CRAM file format are arranged differently than they are arranged in a SAM file (and vice versa). For example, the optional file fields are, at the least, ordered differently in these file formats. In one embodiment, after the mandatory fields are de-converted, the optional fields could be added to the de-converted mandatory fields, which taken together may constitute the original SAM file.

The initial hash value computation provides information that could be used to inform of data corruption that could possibly occur in a de-conversion operation (e.g., de-converting from CRAM to a file originally encoded in SAM), or a corruption caused by a storage issue. For example, the hash value of the de-converted SAM file should equal the hash value of the original SAM file, e.g., that SAM file before conversion to CRAM.

SAM and BAM files are identified by their file extensions. The mandatory fields of the SAM and BAM files are converted into the CRAM file format. A hash value of the mandatory fields of the files converted to the CRAM format is computed and is added to the sequence ID field. This information is stored in metadata. In the case of a SAM file, this involves a conversion from the SAM ASCII file format to the CRAM binary file format. In the case of a BAM file, this involves a conversion from the BAM binary file format to the CRAM binary file format. Using a SAM file, for exemplary purposes only, the resulting computed information that could be described as (CRAM(sequence ID+computed hash value in CRAM of mandatory SAM field data).

A search of sequence IDs is conducted to find possible matches. When two or more possible matches are found based on sequence IDs, the binary data in the CRAM files, e.g., the data in the sequence IDs fields to which the computed hash value of the mandatory fields is compared file-to-file (or among multiple files). As indicated above with regard to the SAM file example, the resulting computed information may be described as (CRAM(sequence ID+computed hash value in CRAM of mandatory SAM field data). Where it is determined that the binary CRAM codes are identical for two or more files, then the computed mandatory fields are not written into storage, e.g., in-line data de-duplication is performed.

Data consolidation is performed among the duplicate data chunks. Duplicate data, e.g., files in two or more formats that contain identical information, is identifiable through the pointers. In one embodiment, the duplicate data chunks are two or more of SAM, BAM and CRAM files that contain identical information. The pointers that are directed to duplicate data chunks are redirected to a single unique stored copy of the data, e.g., one file in one of the file formats. The redundant data chunks are released from storage.

In accordance with present principles, the embodiment in which the optional file fields and metadata are stored in a separate location makes it possible to de-convert a converted file to its original format. This feature is advantageous should it be desirable to use or otherwise maintain a file in the original, pre-conversion format.

Figure 1:
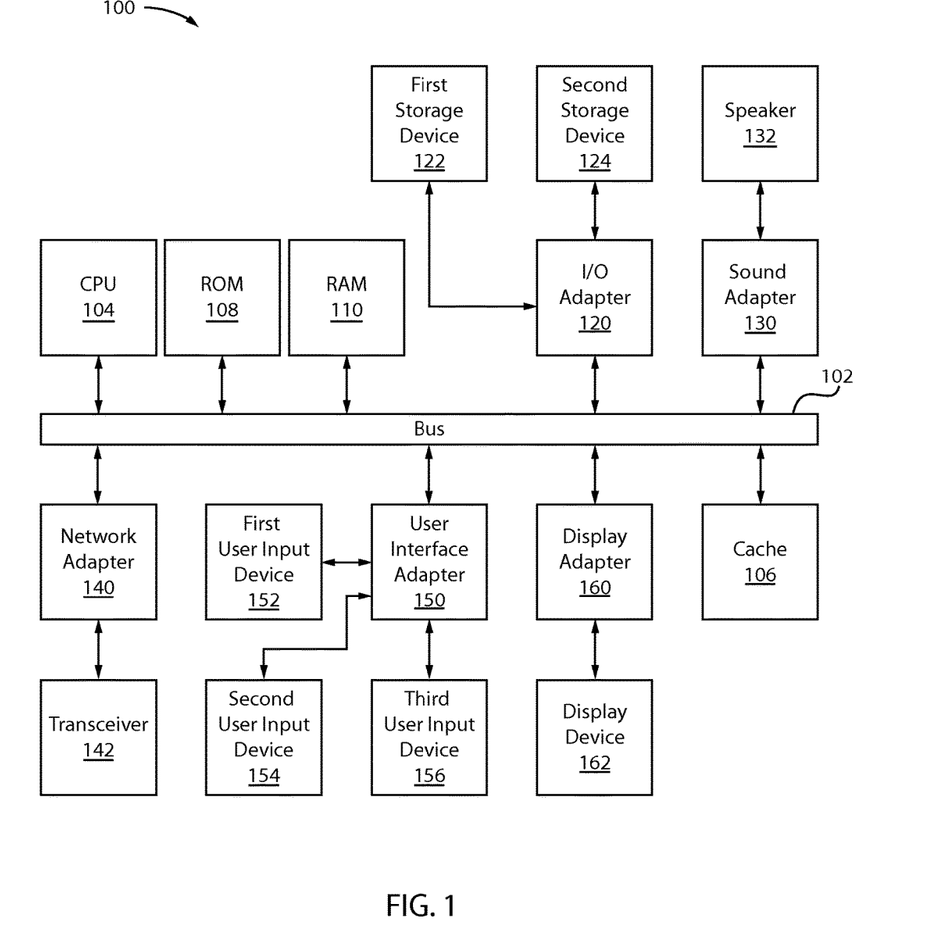
FIG. 1 an exemplary processing system in accordance with the present principles concerning a system and method for de-duplication of genome data files may be applied.

Referring to FIG. 1, an exemplary processing system 100 to which the present principles may be applied is shown. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160 are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154 and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

The processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. It is to be appreciated that the terms processors and controllers can be used interchangeably herein. These and other variations of the processing system 100 are readily contemplated by one of ordinary skill in the art given the teachings of the present principles provided herein.

Figure 2:
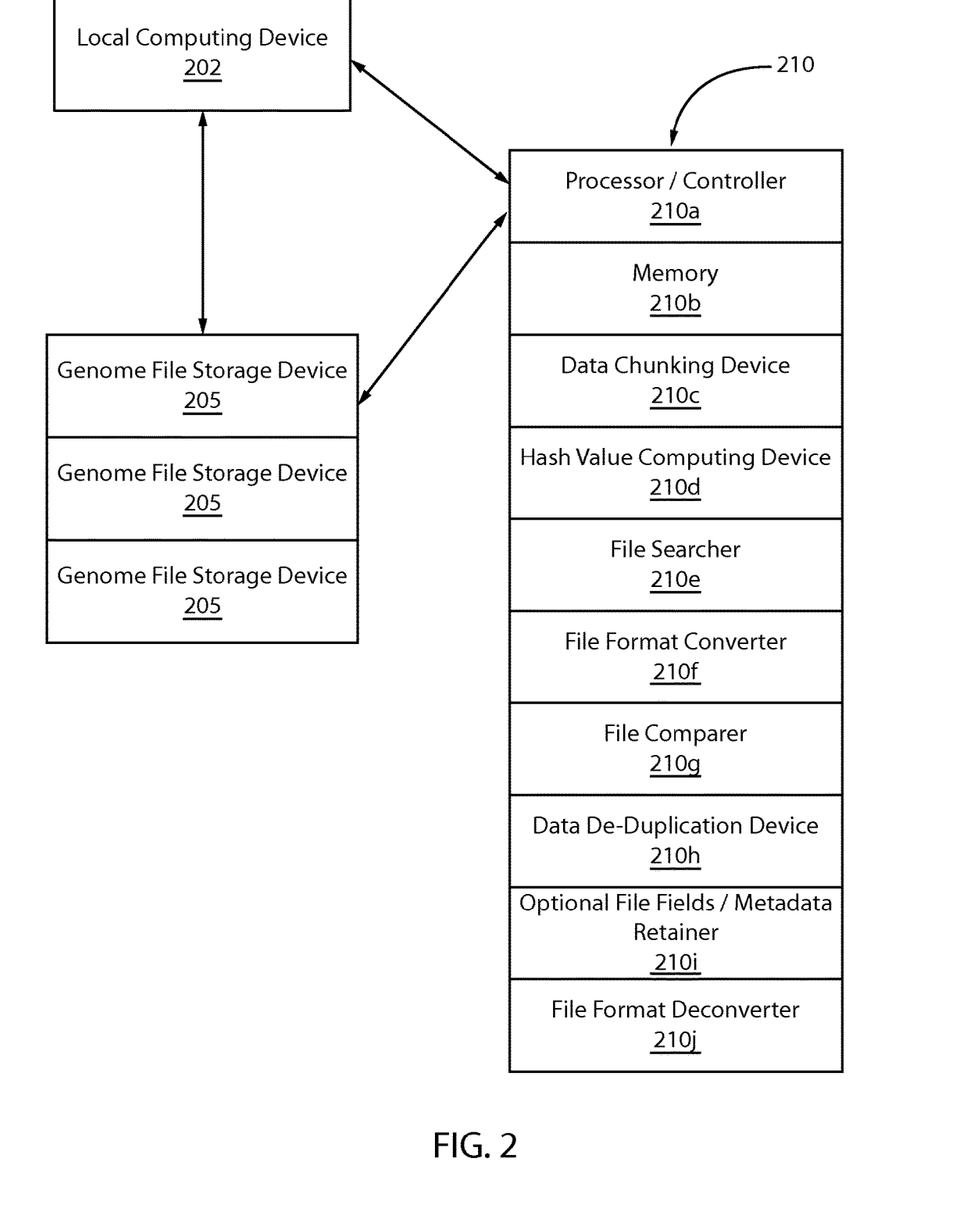
FIG. 2 shows an exemplary system for data-deduplication of genome data stored in different file formats, in accordance with an embodiment of the present principles, and in which system duplicative data across different genome data file formats can be reduced.

Referring to FIG. 2, a system 200 of data de-duplication of genome data in accordance with the present principles is explained. Part or all of processing system 100 may be implemented in one or more of the elements of system 200. Further, it is to be appreciated that processing system 100 may perform at least part of the method described herein including, for example, at least part of method 300 of FIG. 3. Similarly, part or all of system 200 may be used to perform at least part of method 300 of FIG. 3.

System 200 includes one or more storage devices 205 operatively coupled to one or more servers (hereinafter "servers") 210. The one or more storage devices 205 store the genome files that are to be de-duplicated in accordance with present principles. One or more storage devices 205 are similar could be the first and second storage devices 122, 124 of processing system 100 depicted in FIG. 1, and vice versa. The one or more servers 210 are operatively coupled to local computing device 202. In one embodiment, local computing device 654 is operatively coupled to one or more storage devices 205.

Each of the servers 210 can include a processor or controller (hereinafter "controller") 210A, memory 210B, data chunking device 210C, hash value computing device 210D, file searcher 210E, file format converter 210F, file comparer 210G, data de-duplication device 210H, optional file fields/metadata retainer 210I, and file format de-converter 210J. As explained below, the server components 210A to 210H are employed in one system embodiment, and in another system embodiment server components 210A to 210J are employed, e.g., system components 210I and 210J are also employed in this embodiment.

The servers 210 may be within, e.g., local, to a workplace environment, but this does not have to be the case. In another embodiment, the servers 210 can be in the cloud. In yet another embodiment, the servers can be both local and remote, such that the local servers perform some of the functions implicated by the present principles, while the remote servers perform other functions implicated by the present principles.

The data chunking device 210C breaks the data stored on one or more storage devices 205 into chunks. In one embodiment, each chunk is a file, e.g., a SAM file, a BAM file, and/or a CRAM file (e.g., file-based chunking). In another embodiment, block based data chunking format is employed. In yet another embodiment, the format aware data chunking format is employed.

In one embodiment, the hash value computing device 210D computes the hash value of at least the mandatory file fields of the chunks e.g., files. In one other embodiment, the hash value computing device 210D computes the hash value of both of the mandatory file fields and the optional file fields of the chunks e.g., files. The computed hash values of the mandatory fields are added by the hash value computing device 210D to the sequence ID field. In one embodiment, the hash value computation and adding of the computed hash value to the sequence ID is performed on all data files in all formats, e.g., SAM files, CRAM files and BAM files. This provides representations of genome data derived from the original genome data files.

File searcher 210E conducts a search among the chunks, e.g., files, for SAM and BAM files. File format converter 210F converts the mandatory fields of the located SAM and BAM files into the CRAM file format. In one embodiment, this is done without disturbing the original files. Pointers, as needed, are created between the original files and the generated data. Pointers could be established by the data chunking device 210C or other system component, e.g., data de-duplication device 210H.

Hash value computing device 210D computes a hash value of the mandatory fields of the files converted from SAM and BAM to the CRAM file format. The computed hash value is added to the sequence ID field. This provides a representation of genome data in the CRAM file format that is derived from genome data files originally in the SAM and BAM file formats. A representation of genome data in the CRAM file format for files that originated in (and stayed in) the CRAM file format was described above, and thus those files, taken together with the operations described in this and the previous paragraph, provide conformed representations of genome data derived from the original genome data files. In the described embodiment, the conformed representations are in the CRAM file format, though conformed representations could be provided in another file format, e.g., SAM and/or BAM. Pointers, if necessary, are established.

File searcher 210E conducts a search for all files having a common sequence ID, and identifies possible matches from among different files, e.g., files in different file formats, having a common sequence ID.

The file comparer 210G compares, for two or more possible matching files (e.g., files matched based on a common sequence ID), the conformed representations of genome data derived from the original genome data files. File comparer 210G makes the comparison and, when a match is found between the conformed representations, file comparer 210G provides an indication of same, e.g., it indicates that two or more identified files that have been compared and are identical.

Duplicate data is present in the genome file storage system 205 when the compared conformed representations are found to be identical. The data de-duplication device 210H consolidates the stored data and releases duplicate data from storage. When the file comparer 210G identifies a match between the conformed representations of two or more original genome data files, for example, when the binary CRAM codes present in the conformed representations match, the data de-duplication device identifies the relevant data chunks, e.g., files. In one embodiment, this would include the chunks, e.g., original SAM, BAM and CRAM files. The data de-duplication device 210H directs the pointers to a single unique copy of the data. After the pointers are consolidated in this way, the duplicative data and data chunks, e.g., files, are released. In one embodiment, the conformed representations that have been generated are not written into storage, e.g., in-line data de-duplication is performed.

In one embodiment, the original genome data files can be stored in the memory sectors of server memory 210B prior to performing operations, e.g., a first memory sector, and one or more of the data chunking, hash value computing, file searching, file format converting, file comparing, and data de-duplicating can be performed in a different memory sector, e.g., in a second memory sector, a third memory sector, or another memory sector.

Another system embodiment further includes optional file field/metadata retainer 210I and file format de-converter 210J. Here, data chunking device 210C chunks the data as previously described, and optional file field/metadata retainer 210I retrieves the optional file field data from the original files and stores the optional file field data and associated metadata of the original genome data files in the genome file storage system 205. In one embodiment, the optional file field information is copied and stored and the metadata is stored in a fast accessible location.

This system embodiment includes the system components described above, e.g., storage device 205 and the components 210A to 210H of servers 210. Components 210A to 210H of servers 210 otherwise perform the functions above described.

File format de-converter 210J de-converts a converted file, e.g., a file converted to the CRAM format, to its original file format. For example, a CRAM file created from the conversion of a BAM file can be de-converted to a BAM file, and a CRAM file created from the conversion of a SAM file can be de-converted to a SAM file. In this operation, the file format de-converter 210J may use the optional file field information and metadata retrieved and stored by the optional file field/metadata retainer 210I. The stored metadata information concerning the original files, e.g., sequence ID, pointers to the mandatory and original fields, and attribute information for converting and decompressing from the CRAM file format to the SAM file format, could be useful to de-convert to a complete SAM or BAM file. For example, when the file format de-converter 210J de-converts from a CRAM file to a SAM file, the metadata could be used since the optional file fields in the CRAM file format are arranged differently than they are arranged in a SAM file (and vice versa). For example, the optional file fields are, at the least, ordered differently in these file formats. In one embodiment, after the mandatory fields are de-converted, the optional fields could be added by file format de-converter 210J to the de-converted mandatory fields, which taken together may constitute the original SAM file.

In one exemplary embodiment, the file format de-converter 210J de-converts a CRAM file to a BAM file. In another embodiment, the de-conversion is from a CRAM file to SAM file.

In one embodiment, one or more of the optional file fields and metadata retention and the file de-conversion can be performed in a memory sector different from the first memory sector where the original genome data files are stored, e.g., in a second memory sector, a third memory sector, or other memory sector.

The preceding description is intended to merely be illustrative. Thus, one of ordinary skill in the art will contemplate various other ways for visualizing distribution of throughput and response time in a computing environment, while maintaining the spirit of the present principles.

The memory 210B stores data relating to the present principles including, but not limited to, the instructions for processing the aforementioned files and the data generated in accordance with the present principles. In the case of the data chunking device 210C, hash value computing device 210D, file searcher 210E, file format converter 210F, file comparer 210G, data de-duplication device 210H, optional file fields/metadata retainer 210I, and file format de-converter 210J, these components are implemented as software or implemented in part in software. Such software can be stored in the memory 210B. However, these components can also be implemented as least in part in hardware, including standalone devices, boards, integrated circuits, and so forth. In an embodiment, at least one of the data chunking device 210C, hash value computing device 210D, file searcher 210E, file format converter 210F, file comparer 210G, data de-duplication device 210H, optional file fields/metadata retainer 210I, and file format de-converter 210J are implemented as application specific integrated circuits (ASICS). These and variations of the elements of system 200 are readily contemplated by one of ordinary skill in the art given the teachings of the present principles provided herein, while maintaining the spirit of the present principles.

Figure 3:
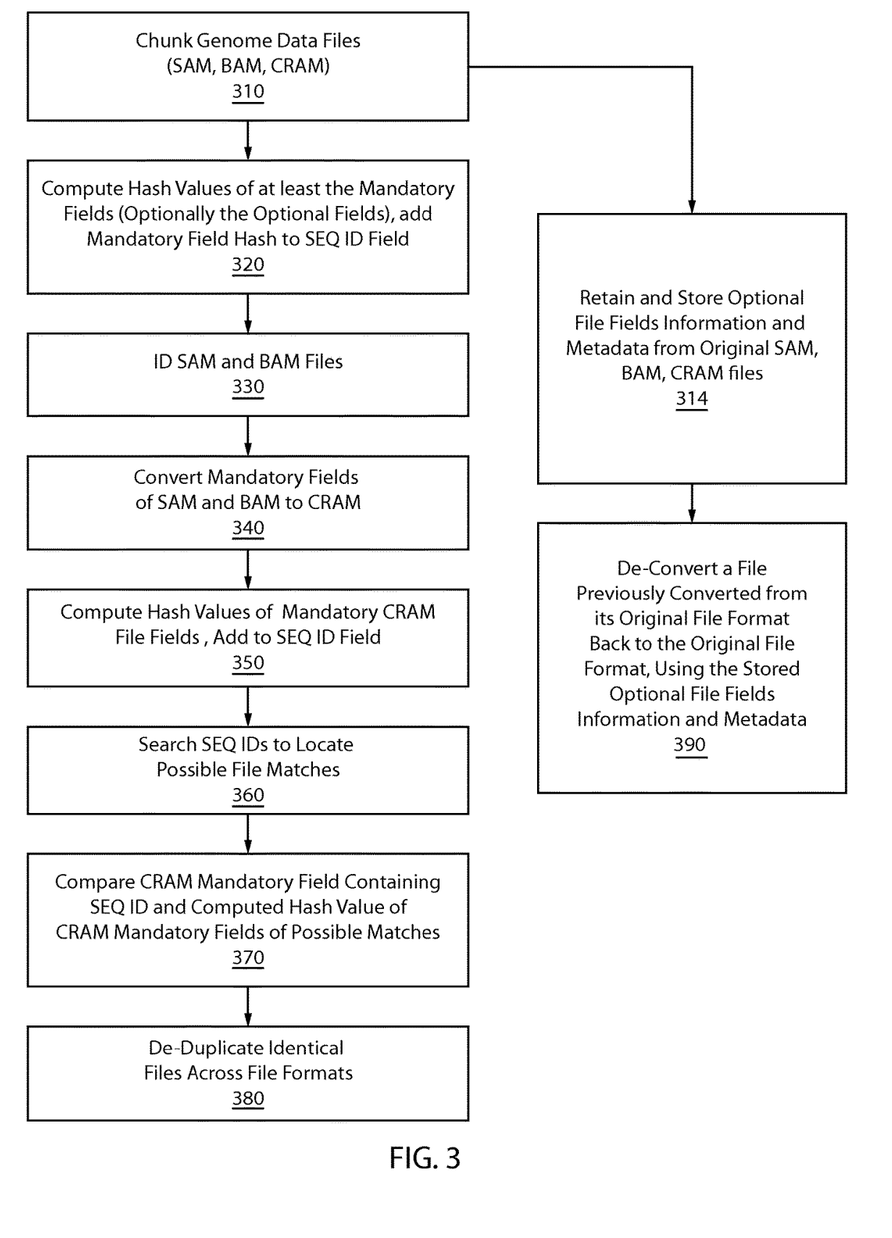
FIG. 3 is a block diagram showing an exemplary method of data-deduplication of genome data stored in different file formats, in accordance with an embodiment of the present principles, and through which method duplicative data across different genome data file formats can be reduced.

Referring to FIG. 3, an exemplary method 300 of data de-duplication of genome data stored in different file formats, in accordance with an embodiment of the present principles, is shown. Method 300 can be performed in accordance with system 200.

In block 310, the genome data files, which contain mandatory fields and may contain optional fields, are subjected to chunking. The files can be chunked in accordance with a chunking format, e.g., file based chunking, block based chunking, and format aware chunking. In one embodiment, the genome data files are SAM, BAM and CRAM files.

In block 320, the hash values of at least the mandatory file fields of the chunks, e.g., files, are computed. In another embodiment, the hash values of the optional file fields are also computed. The mandatory fields contain information concerning the alignment of the sequence. The computed hash values are added to the sequence ID field and stored in metadata. The optional fields contain additional information about the sequence.

In block 330, SAM and BAM files are identified. In one embodiment, SAM and BAM files are identified by their file extensions (e.g., .sam and .bam).

In block 340, the mandatory fields of the SAM and BAM files are converted to the CRAM file format.

In block 350, the hash values of the converted CRAM mandatory fields are computed and are added to the sequence ID field (CRAM(SEQ ID+mandatory field hash)).

In block 360, a search is conducted of sequence IDs to find possible file matches.

In block 370, if a possible match is found through the search of sequence IDs, a comparison of the CRAM(SEQ ID+mandatory field hash) for the possible matching files is made. E.g., a comparison of conformed representations of the original genome data files is made.

If, in block 370, the possible matching files are found to in fact be identical, then the new mandatory filed information (e.g., the CRAM(SEQ ID+mandatory field hash) is not written into storage (e.g., in-line data de-duplication is practiced).

In block 380, the pointers among the duplicate file chunks, e.g., files, are directed to a single unique copy of the data, e.g., file and duplicate copies of the data, e.g., files, are released from storage.

In block 314, the optional file fields are retrieved from an original genome file. The retrieved data may be separated from the mandatory file fields of the original genome file, or it may be copied from the original file and stored. This step pertains to a second method embodying present principles.

In block 390, a file converted from its original genome data file format to another file format is de-converted to its original file format. The optional file fields and the metadata are used to de-convert the file to its original file format.

There are several advantages the flow from implementing the present principles over conventional solutions. For example, NA12878, a genome sequenced by the 1000 Genomes Project, needs 1,354 GB (1.354 TB) of storage for CRAM, BAM, and SAM files. SAM files need 966 GB of storage, BAM files need 233 GB of storage, and CRAM files need 155 GB of storage. In accordance with present principles, the required storage for NA 12878 could be reduced to 155 GB—the storage size for the CRAM files. Stored data could be reduced by 88.6%, e.g., 1,199 GB (1.199 TB).

It may be that CRAM is the most efficient file storage system of the three formats, perhaps due to the compression scheme it employs. In accordance with present principles, the search determines whether, among duplicate files, a CRAM file exists. In the event a CRAM file does exist, the pointers could be directed to the CRAM file as the unique copy to be retained, with the larger SAM and BAM files being released. Should no CRAM file exist among duplicates, then a SAM or BAM file could be retained. It may be that the BAM file would be smaller than the SAM file, indicating that keeping the BAM file would be preferred.

While the present disclosure includes a detailed description on cloud computing, it should be understood that implementation of the subject matter described herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and personal digital assistants (PDAs)).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 4:
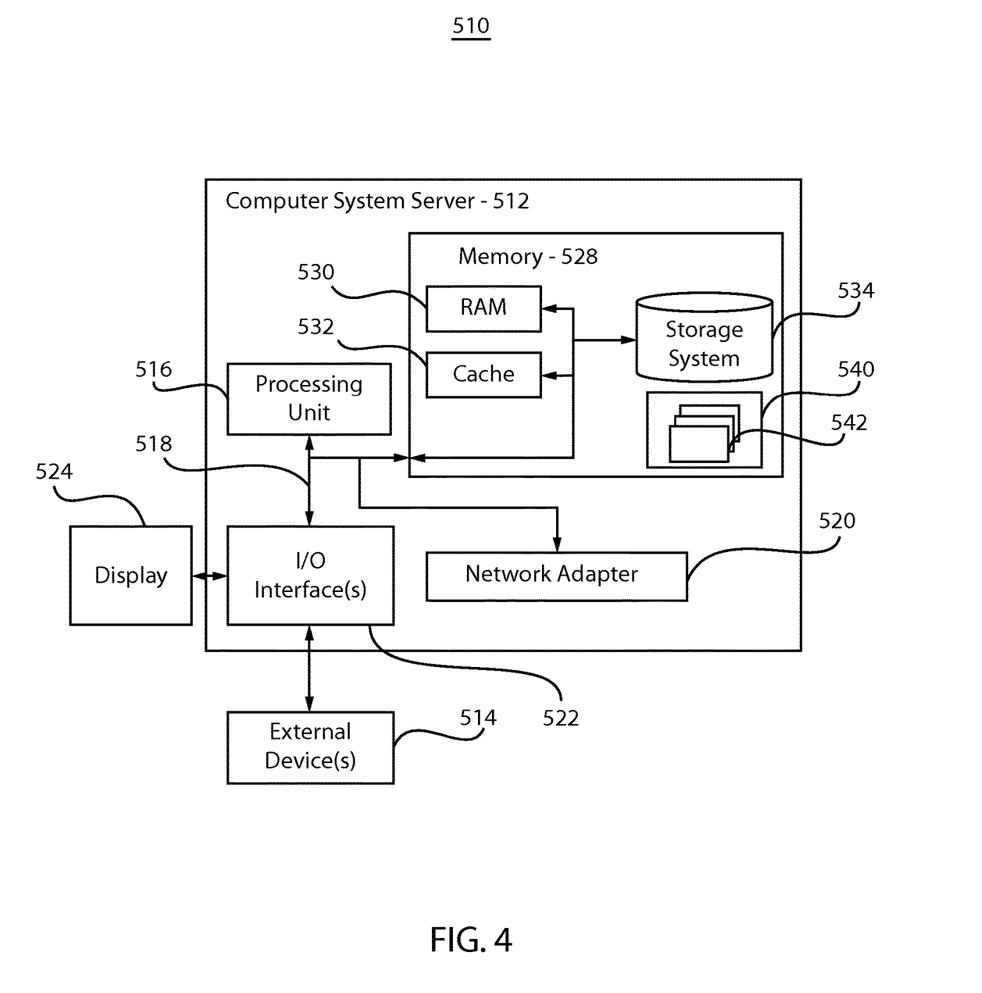
FIG. 4 shows an exemplary cloud computing node in accordance with an embodiment representative of a node for requesting cloud computing services.

Referring now to FIG. 4, a schematic of an example of a cloud computing node 510 is shown. Cloud computing node 510 is only one example of a suitable cloud computing node and is not intended to suggest any limitation as to the scope of use or functionality of embodiments of the invention described herein. Regardless, cloud computing node 510 is capable of being implemented and/or performing any of the functionality set forth hereinabove.

In cloud computing node 510 there is a computer system/server 512, which is operational with numerous other general purpose or special purpose computing system environments or configurations. Examples of well-known computing systems, environments, and/or configurations that may be suitable for use with computer system/server 512 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 512 may be described in the general context of computer system executable instructions, such as program modules, being executed by a computer system. Generally, program modules may include routines, programs, objects, components, logic, data structures, and so on that perform particular tasks or implement particular abstract data types. Computer system/server 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 512 in cloud computing node 510 is shown in the form of a general-purpose computing device. The components of computer system/server 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 512 typically includes a variety of computer system readable media. Such media may be any available media that is accessible by computer system/server 512, and it includes both volatile and non-volatile media, removable and non-removable media.

System memory 528 can include computer system readable media in the form of volatile memory, such as random access memory (RAM) 530 and/or cache memory 532. Computer system/server 512 may further include other removable/non-removable, volatile/non-volatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system/server 512 may also communicate with one or more external devices 514 such as a keyboard, a pointing device, a display 524, etc.; one or more devices that enable a user to interact with computer system/server 512; and/or any devices (e.g., network card, modem, etc.) that enable computer system/server 512 to communicate with one or more other computing devices. Such communication can occur via Input/Output (I/O) interfaces 522. Still yet, computer system/server 512 can communicate with one or more networks such as a local area network (LAN), a general wide area network (WAN), and/or a public network (e.g., the Internet) via network adapter 520. As depicted, network adapter 520 communicates with the other components of computer system/server 512 via bus 518. It should be understood that although not shown, other hardware and/or software components could be used in conjunction with computer system/server 512. Examples include, but are not limited to: microcode, device drivers, redundant processing units, external disk drive arrays, RAID systems, tape drives, and data archival storage systems, etc.

Figure 5:
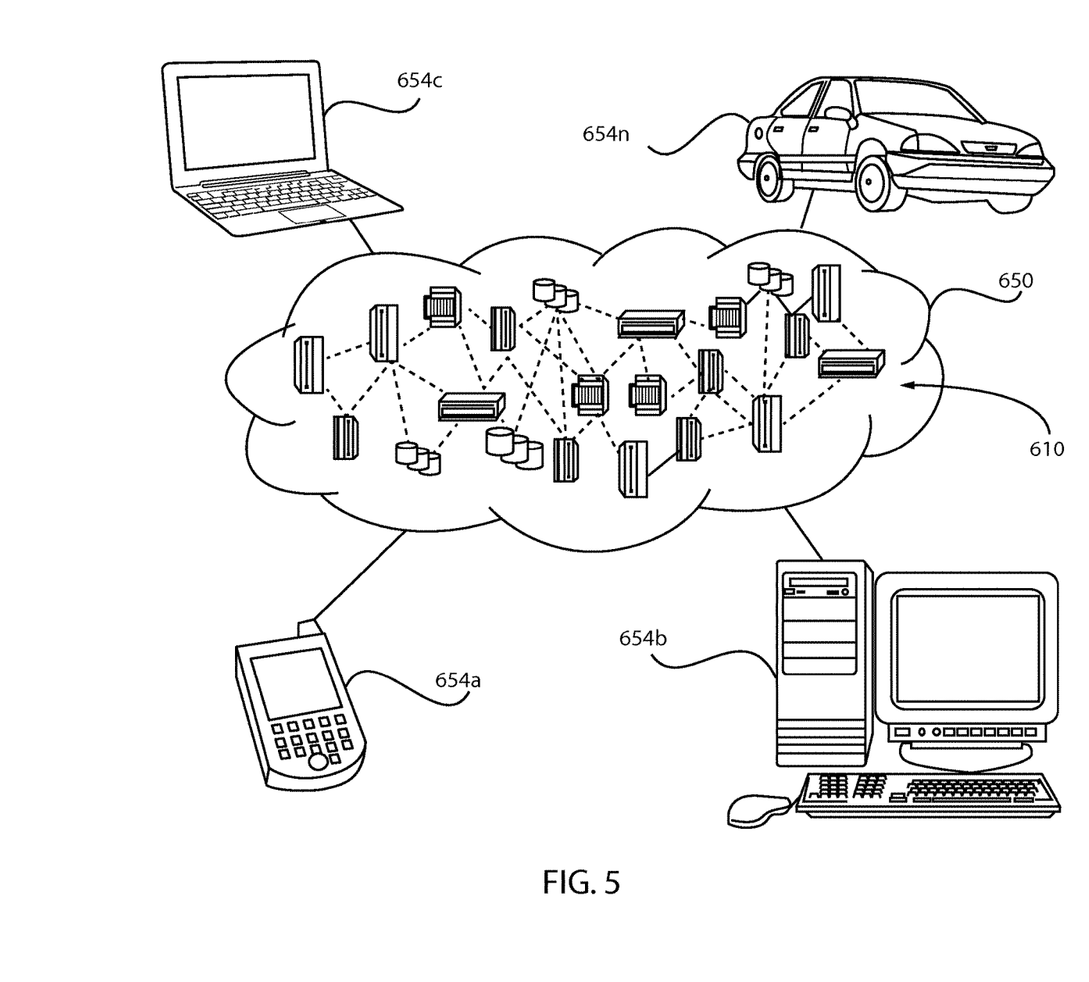
FIG. 5 shows an exemplary cloud computing environment in accordance with an embodiment of the present principles that is representative of a computing environment in which present principles may be applied.

Referring now to FIG. 5, illustrative cloud computing environment 650 is depicted. As shown, cloud computing environment 650 comprises one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N are intended to be illustrative only and that computing nodes 610 and cloud computing environment 650 can communicate with any type of computerized device over any type of network and/or network addressable connection (e.g., using a web browser). Local computing device 202 of FIG. 2 is representative of a computing node 610.

Figure 6:
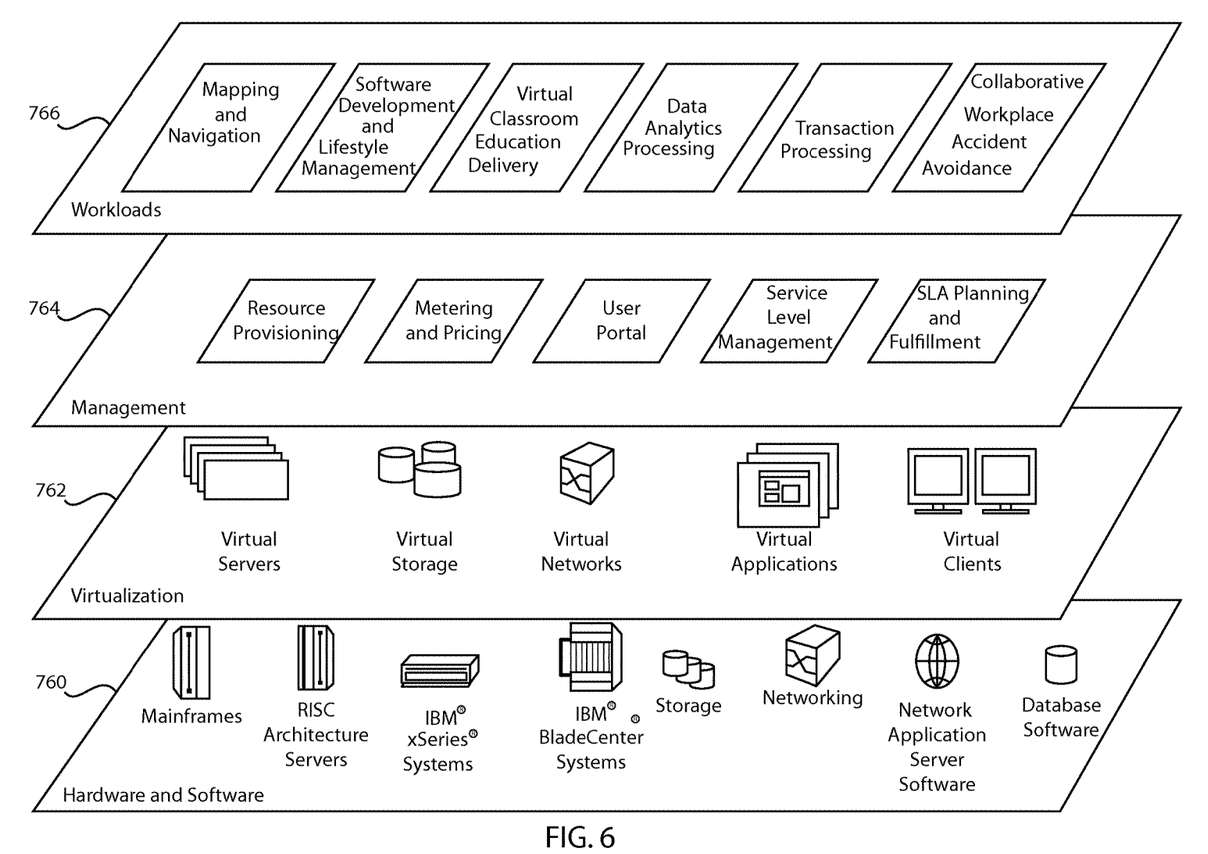
FIG. 6 shows exemplary abstraction model layers provided by cloud computing environment that could be subject to a visualized representation embodying the present principles.

FIG. 6 shows a set of functional abstraction layers provided by cloud computing environment 650. It should be understood in advance that the components, layers, and functions shown in FIG. 6 are intended to be illustrative only and embodiments of the invention are not limited thereto. As depicted, the following layers and corresponding functions are provided:

Hardware and software layer 760 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 762 provides an abstraction layer from which the following examples of virtual entities may be provided: virtual servers; virtual storage; virtual networks, including virtual private networks; virtual applications and operating systems; and virtual clients.

In one example, management layer 764 may provide the functions described below. Resource provisioning provides dynamic procurement of computing resources and other resources that are utilized to perform tasks within the cloud computing environment. Metering and pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 766 provides examples of functionality for which the cloud computing environment may be utilized. Examples of workloads and functions which may be provided from this layer include: mapping and navigation; software development and lifecycle management; virtual classroom education delivery; data analytics processing; transaction processing; and collaborative workplace accident avoidance.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of data-deduplication of genome data stored in different file formats which are intended to be illustrative and not limiting, it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for de-duplicating genome data comprising:
    storing, in a computer memory, genome data as original genome data files in different original genome data file formats;
    generating respective representations of the original genome data files based on data derived from at least mandatory file fields of the original genome data files;

converting any of the original genome data files determined to not be in a selected genome data file format into the selected genome data file format, thereby creating respective converted genome data files;

creating, in the selected genome data file format, conformed representations representing respective ones of the original genome data files;

comparing the conformed representations;

identifying duplicates of the original genome data files among the conformed representations based on the comparison; and releasing at least one of the duplicates of the original genome data files, wherein one or more of the creating, comparing, identifying, and releasing are performed by at least one hardware processor.

2. The method of claim 1, wherein generating the representations of the original genome data files further comprises:

computing hash values of the mandatory file fields; and adding the computed hash values of the mandatory file fields to sequence identification fields to create the representations of the original genome data files.

3. The method of claim 1, wherein generating the representations of the original genome data files further comprises:

computing hash values of the mandatory file fields and optional file fields of the original genome data files; and adding the computed hash values to sequence identification fields to create the representations of the original genome data files.

4. The method of claim 1, wherein the releasing of at least one of the duplicates of the original genome data files further comprises:

identifying pointers to the duplicates of the original genome data files;

directing the pointers to one of the original genome data files among the duplicates of the original genome data files; and releasing remaining duplicates of the original genome data files.

5. The method of claim 1, further comprising breaking the genome data into data chunks.

6. The method of claim 1, further comprising storing optional file fields and original file metadata of the original genome data files.

7. The method of claim 6, further comprising:

de-converting the converted genome data files to their respective original genome data file formats, and recreating the original genome data files with the stored optional file fields and stored original file metadata.

8. The method of claim 1, further comprising searching for files having a common sequence identification field, wherein the comparison is performed between files having the common sequence identification field.

9. A system for de-duplicating genome data comprising:

one or more servers having a processor including memory for storing original genome data files and for collecting information comprising at least mandatory file fields from original genome data files in different original genome data file formats;

the processor being configured to perform an operation, the operation comprising:

generating respective representations of the original genome data files based on data derived from at least the mandatory file fields of the original genome data files;

converting any of the original genome data files determined to not be in a selected genome data file format into the selected genome data file format, thereby creating respective converted genome data files;

creating in the selected genome data file format, conformed representations representing respective ones of the original genome data files;

comparing the conformed representations;

identifying duplicates of the original genome data files among the conformed representations; and releasing at least one of the duplicates of the original genome data files.

10. The system of claim 9, wherein generating the representations of the original genome data files further comprises:

computing hash values of at least the mandatory file fields; and adding the computed hash values to sequence identification fields of the original genome data files.

11. The system of claim 10, wherein comparing the conformed representations, further comprises comparing the computed hash values that have been added to the sequence identification fields.

12. The system of claim 9, wherein the operation further comprises breaking the genome data into chunks.

13. The system of claim 9, wherein the operation further comprises searching for files having a common sequence identification field, and wherein the comparison is performed between files having the common sequence identification field.

14. The system of claim 9, wherein the operation further comprises storing optional file fields original file metadata of the original genome data files.

15. The system of claim 14, wherein the operation further comprises de-converting the converted genome data file to their respective original genome data file formats, and recreating the original genome data files with the stored optional file fields and stored original file metadata.

16. The system of claim 9, wherein the releasing of at least one of the duplicates of the original genome data files further comprises:

identifying pointers to the duplicates of the original genome data files;

directing the pointers to one of the original genome data files among the duplicates of the original genome data files; and releasing remaining duplicates of the original genome data files.

17. The system of claim 9, wherein generating the representations of the original genome data files further comprises:

computing hash values of the mandatory file fields and optional file fields of the original genome data files; and adding the computed hash values to sequence identification fields of the original genome data files to create the representations of the original genome data files.

18. A computer program product for de-duplicating genome data , the computer program product comprising a non-transitory computer readable storage medium having program instructions embodied therewith, the program instructions being executable by a computer to cause the computer to perform a method comprising:

from genome data stored as original genome data files in different original genome data file formats, generating respective representations of the original genome data files based on data derived from at least mandatory file fields of the original genome data files;

converting any of the original genome data files determined to not be in a selected genome data file format into the selected genome data file format, thereby creating respective converted genome data files;

creating, in the selected genome data file format, conformed representations representing respective ones of the original genome data files;

comparing the conformed representations;

identifying duplicates of the original genome data files among the conformed representations of genome data based on the comparison; and releasing at least one of the duplicates of the original genome data files.

19. The computer program product of claim 18, wherein generating the representations of the original genome data files further comprises:

computing hash values of at least the mandatory file fields; and adding the computed hash values to sequence identification fields to create the representations of the original genome data files.

20. The computer program product of claim 18, wherein the method further comprises breaking the genome data into chunks.

* * * * *